United States Patent [19]

Tepic et al.

[11] Patent Number: 5,733,287
[45] Date of Patent: Mar. 31, 1998

[54] BONE PLATE

[75] Inventors: Slobodan Tepic; Stephen Bresina, both of Davos, Switzerland

[73] Assignee: Synthes (U.S.A.), Paoli, Pa.

[21] Appl. No.: 638,689

[22] Filed: Apr. 26, 1996

Related U.S. Application Data

[63] Continuation of Ser. No. 249,238, May 24, 1994, abandoned.

[51] Int. Cl.⁶ .................................................. A61B 17/80
[52] U.S. Cl. ................................................................ 606/69
[58] Field of Search ........................... 606/69, 70, 71, 606/61, 60; D24/145, 155, 140; 428/573; 411/84, 87, 88, 101, 457, 461

[56] References Cited

U.S. PATENT DOCUMENTS

| D. 288,236 | 2/1987 | Homsy et al. ............ D24/155 |
| 3,695,259 | 10/1972 | Yost .............................. 606/69 |
| 4,297,993 | 11/1981 | Härle ............................ 606/70 |
| 4,493,317 | 1/1985 | Klaue ........................... 606/69 |
| 5,002,544 | 3/1991 | Klaue et al. ................. 606/69 |

FOREIGN PATENT DOCUMENTS

| A-173267 | 3/1986 | European Pat. Off. . |
| A-318762 | 6/1989 | European Pat. Off. . |
| U-9208234 | 11/1992 | Germany . |

*Primary Examiner*—Guy V. Tucker
*Attorney, Agent, or Firm*—Fish & Richardson P.C.

[57] ABSTRACT

This bone plate has an upper side, a lower side for bone contact, two longitudinal sides, a longitudinal center line and a plurality of screw holes extending from said upper to said lower side.

The surface of said upper side around said screw holes is designed as a depressed area with regard to the rest of said upper side and the side edge of said depressed area is running approximately parallel to said longitudinal sides.

The removal of material is effected at strategic locations of the bone plate in order to reduce the peak stresses.

17 Claims, 9 Drawing Sheets

BONE PLATE

This is a continuation of application Ser. No. 08/249,238 filed on May 24, 1994 now abandoned.

FIELD OF THE INVENTION

This invention relates to a bone plate with an upper side, a lower side for bone contact, two transverse sides, two longitudinal sides, a longitudinal center line, a plurality of screw holes extending from said upper to said lower side, said surface of said upper side around said screw holes being designed as a depressed area with regard to the rest of said upper side.

BACKGROUND ART

Strength reduction caused by stress concentration around screw holes of the bone plate utilized to lock the implant to the bone with screws or bolts can lead to failure of the implant. The conventional approach for improving the strength of the bone plate is to increase the dimensions of the critical section or add material around the hole.

The disadvantages of these known modifications are increased invasiveness of the implant. Furthermore, in the surgical application for which the bone plates are designed, it is not always possible to increase the dimensions at the critical sections of the bone plate.

A minimal amount of tissue disturbance would be desirable.

SUMMARY OF THE INVENTION

The invention as claimed aims at solving the above described problems by providing a plate having the same over-all dimensions with less material. The removal of material is effected at strategic locations of the bone plate in order to reduce the peak stresses.

With a beam (approximating the bone plate body) loaded in bending, the stresses can be reduced at the edge of the screw holes by bringing the hole closer to the neutral longitudinal axis of the beam. This is done by removing material from the surface of said upper side around said screw holes, e.g. by cutting a continuous or discontinuous longitudinal groove. The depth of the groove is optimized when the stresses at point A (edge of the screw hole) and point B (edge of the groove at the screw hole) are equal.

In a further embodiment of the invention—where transverse cuts are present on the under surface of the implant—the cross-section between the screw holes is not decreased. Therefore, the groove on the top surface is made discontinuous with smooth transition in and out of the hole.

In a further embodiment of the invention—where the undersurface of the bone plate has a concave shape—the height of contact between the screw hole and the bone plate was reduced along the longitudinal center line of the bone plate with a flat groove. Material should not be reduced along the longitudinal center line of the bone plate. With an optimized profile on a circular tool, an overcut is produced that permits a smooth transition into and out of the screw hole; reduces the stress along the edge of the screw hole; and maintains full contact height with the screw along the longitudinal center line of the bone plate.

The various features of novelty which characterize the invention are pointed out with particularity in the claims annexed to and forming part of this disclosure. For the better understanding of the invention, its operating advantages and specific objects attained by its use, reference should be had to the accompanying drawings, examples and descriptive matter in which are illustrated and described preferred embodiments of the invention.

DETAILED DESCRIPTION OF THE INVENTION

Figure 1:
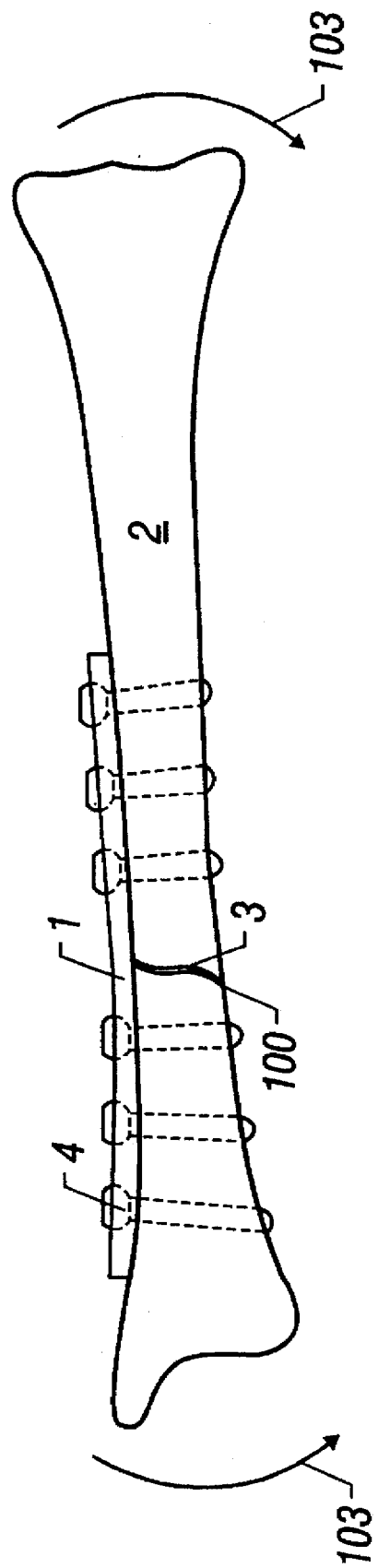
FIG. 1 is a schematic view of a fractured bone held together with a bone plate.

Referring to FIG. 1, a conventional bone plate 1 for treatment of bone fractures 3 is fixed to the bone 2 by means of a number of screws 4. The bending moment—indicated by arrows 103—applied to the bone 2 by muscle forces causes tension on one side of the bone 2 while the other side is loaded in compression. Typically, the plate 1 is applied to the tension side of the bone 2. Therefore, the plate 1 is loaded in either tension or a combination of bending and tension depending on the amount of contact between the bone 2 halves at point 100.

Figure 2:
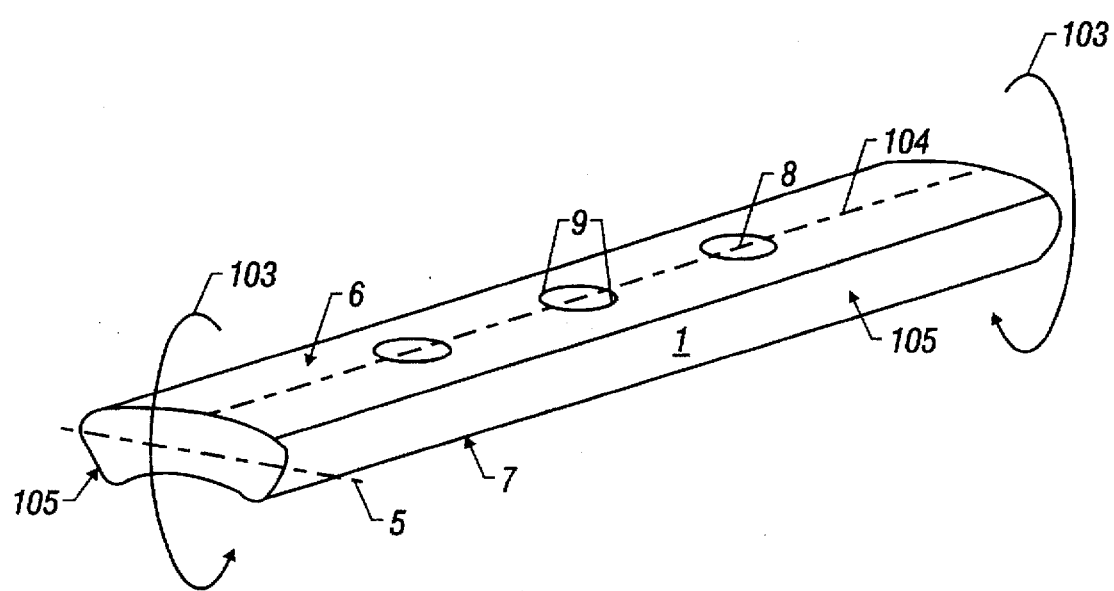
FIG. 2 is a perspective view of a bone plate.

The plate 1 shown in FIG. 2 is loaded in bending as indicated by arrows 103. Longitudinal center line 104 of the plate 1 is shown on the top surface 6. Longitudinal sides of the plate 1 are indicated by numerals 105. The highest stresses occur at the furthest distance in a cross section from the neutral axis 5 which is at the top surface 6 or the bottom surface 7. The holes 8 cause stress concentrations at the edge of the holes 9 which increase the tensile stress on the upper surface 6 by a factor of between 2 to 3.

Figure 3:
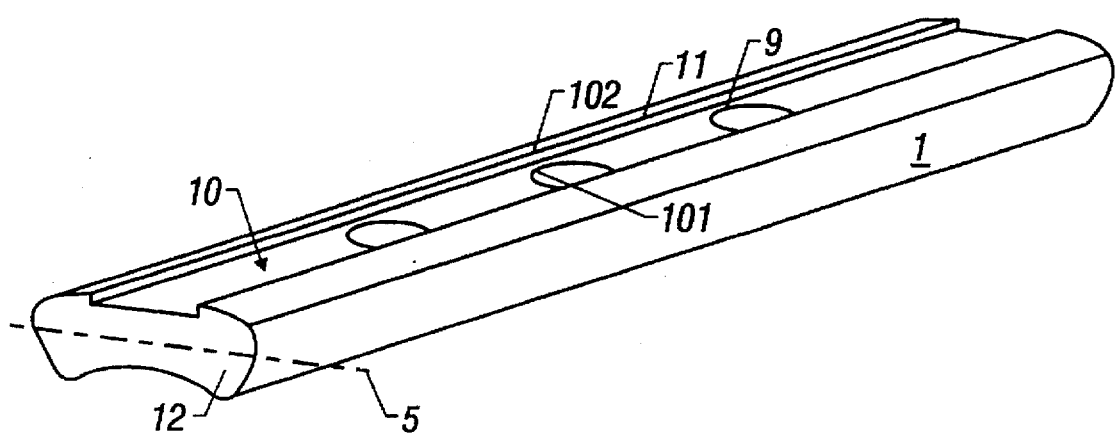
FIG. 3 is a perspective view of a bone plate with a longitudinal groove removed.

Referring to FIG. 3, the stresses can be reduced at the edge of the holes 9 by bringing the edge of the hole 9 closer to the neutral axis 5 of the cross section of the plate. A groove 10 cut into the plate 1 brings the edge of the hole 9 closer to the neutral axis 5. The depth of the groove is optimized when the stresses at point 101 (edge of hole 9) and point 102 (edge of groove 11 at hole) are equal. If the groove is made deeper than this, the loss in strength due to the decrease of the cross-sectional area 12 becomes more significant than the gain made by reducing the stress at the hole edge 9.

Figure 4:
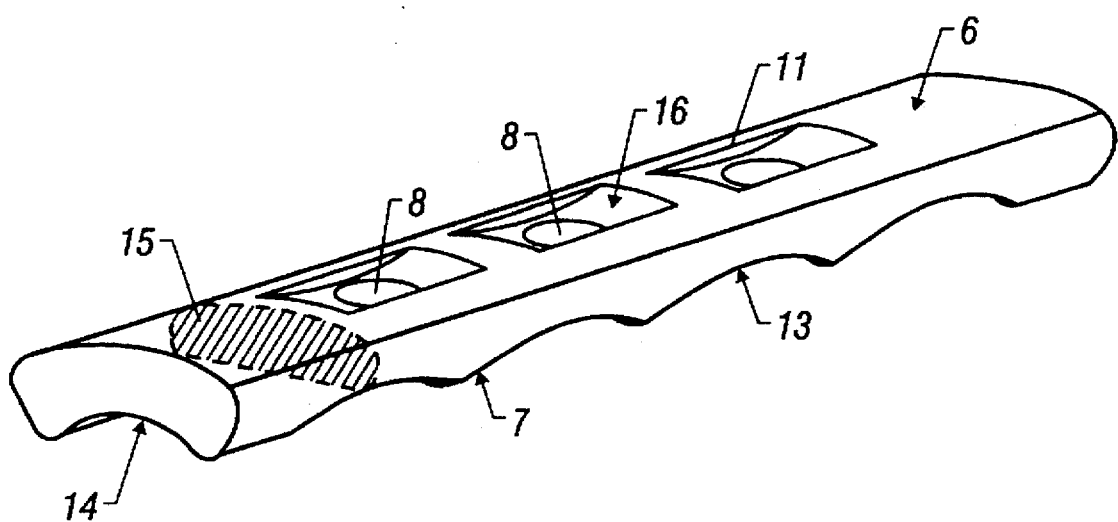
FIG. 4 is a perspective view of the bone plate according to the invention with short grooves only in the hole region.

FIG. 4 shows an embodiment of the invention in which the plate has transverse cuts 13 and a longitudinal cut 14 on the lower surface 7 to reduce contact between the plate and bone. Due to the transverse undercuts 13, the cross-section 15 between the holes is already significantly reduced and should not be decreased further by an additional groove 10 on the upper surface 6 as in the embodiment according to FIG. 3. Therefore, the groove on the upper surface 6 is made discontinuous into short segmental grooves 16 providing a smooth transition into and out of the holes 8.

Figure 5:
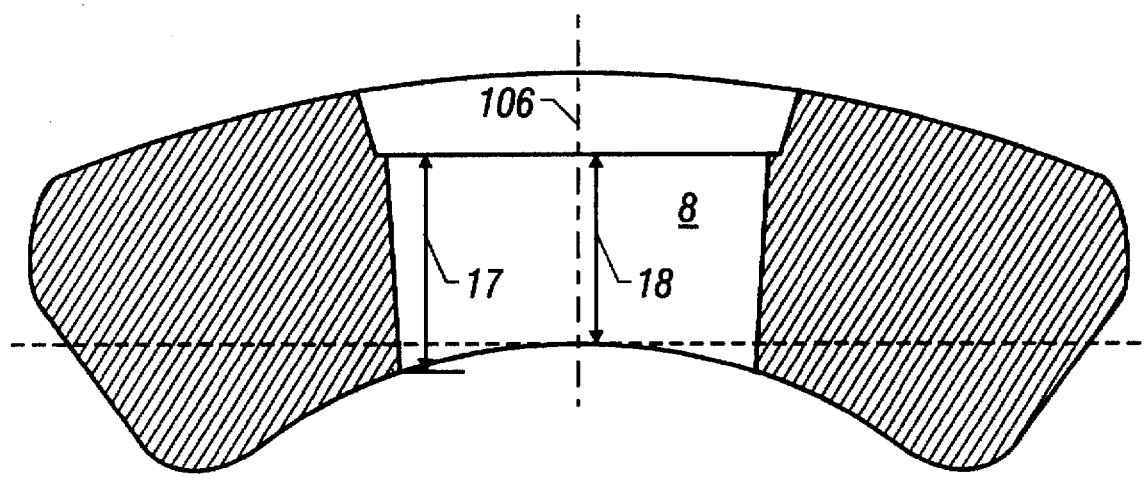
FIG. 5 is a transverse section perpendicular to the longitudinal axis of the bone plate of FIG. 4 through the center of a screw hole.

As shown in FIG. 5, along the centerline 106 the height of contact between the screw and the hole 8 is less than the height 17 at the edge of the hole. This could lead to instability of the screw in the longitudinal axis of the plate. Therefore, material should not be removed along the longitudinal centerline of the plate.

Figure 6:
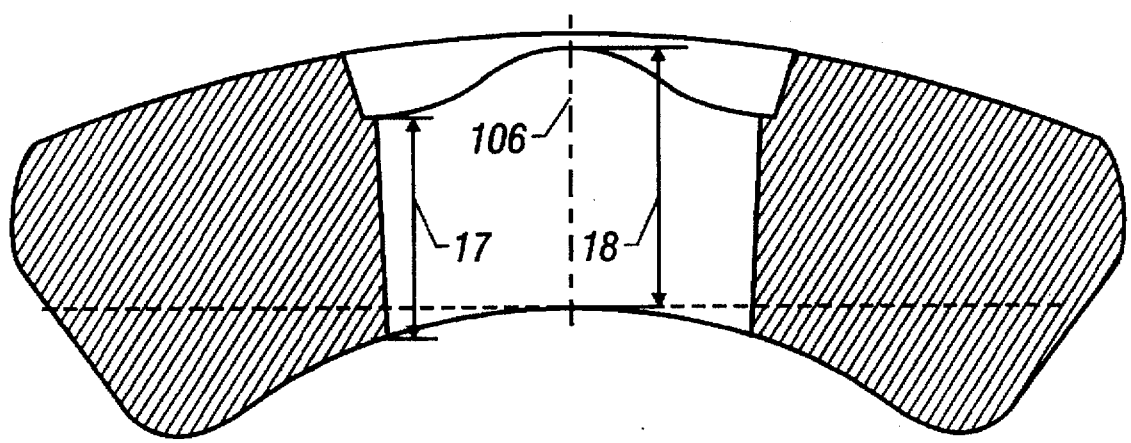
FIG. 6 is a transverse section of the bone plate analogous to FIG. 5 but with a modified groove profile.

With the optimized profile on a circular tool, the cross section shown in FIG. 6 is created. With this cross section, the height of contact 18 along the centerline 106 is at least equal to the height 17 at the edge of the hole.

Figure 7:
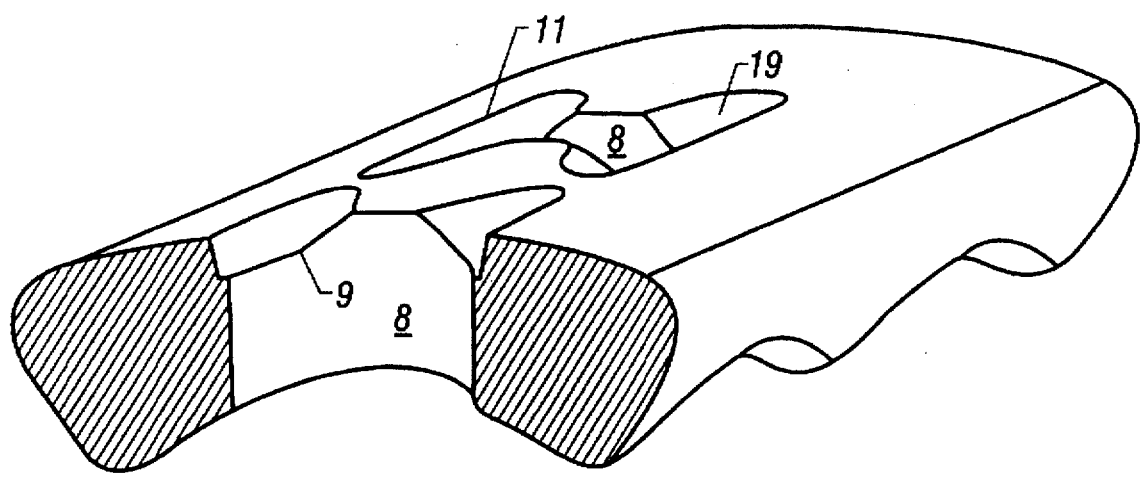
FIG. 7 perspective view, including transverse section through a plate hole with special over-cuts.
Figure 8:
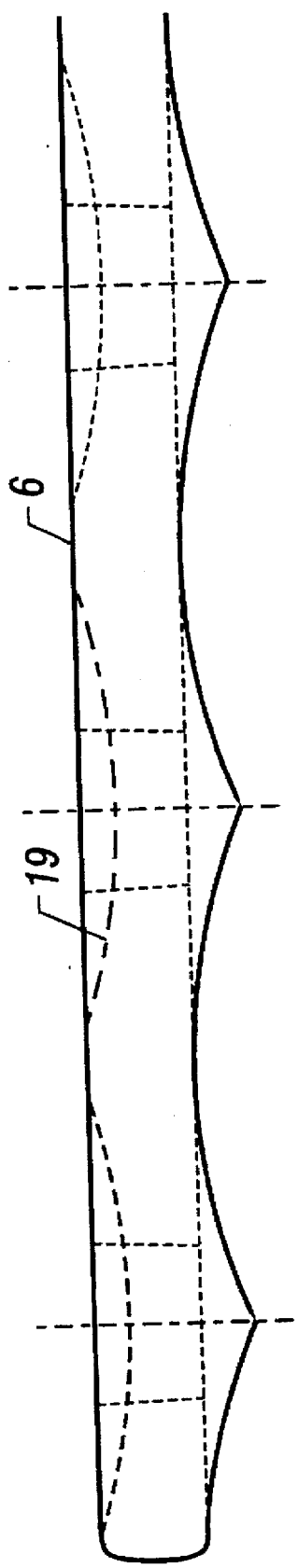
FIG. 8 is a lateral view of the bone plate of FIG. 7.
Figure 9:
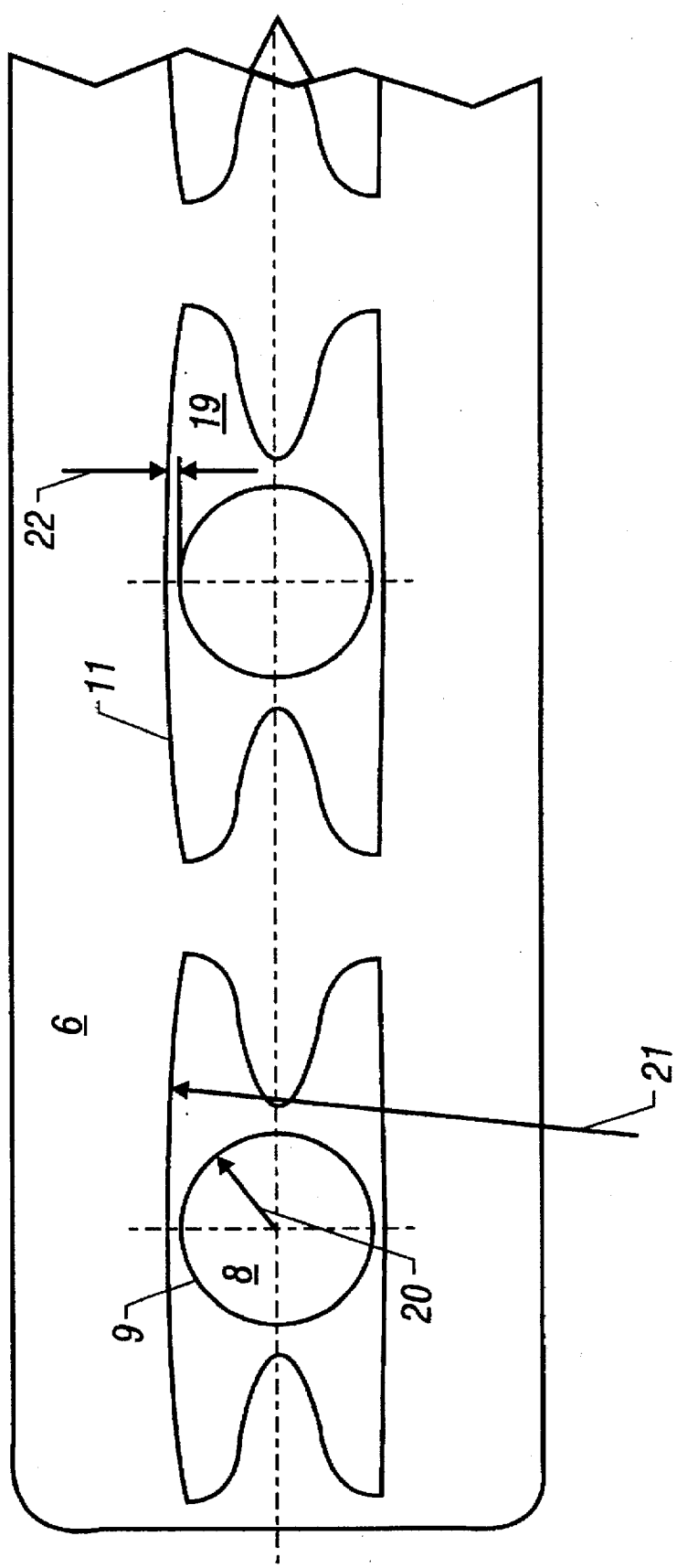
FIG. 9 is a top view of the bone plate of FIG. 7.

A further embodiment of the invention is shown in FIGS. 7–9, wherein the plate is provided with special overcuts in the form of depressed areas 19 that permit a smooth transition into and out of the hole 8 and still reduce the stress along the edge of the hole 9. The depth of the recessed areas 19 should purposefully be in the range of 0.2 to 2.0 mm and are designed in such a way that maximum stress at remaining surface of said upper side near said holes is approximately equal to the maximum stress at edges of said holes within said depressed areas.

Referring to FIG. 9 curvature $C_2$ of the hole 8 is defined as the ratio $1/r_2$, where $r_2$ is the radius 20 of the hole 8. Correspondingly, curvature $C_1$ is equal to the ratio $1/r_1$, where $r_1$ is the radius 21 of the edge 11 of the depressed area 19. Distance between the edge 11 of the depressed area 19 and the edge 9 of the hole 8 is indicated by arrows 22 and should be less than 1.0 mm preferably in the range of 0.1 to 1.0 mm. Curvature $C_1$ should be smaller than 60%, preferably smaller than 10% of the curvature $C_2$.

While the foregoing description and drawings represent the preferred embodiments of the present invention, it will be obvious for those skilled in the art that various changes and modifications may be made therein without departing from the true spirit and scope of the present invention.

We claim:

1. Bone plate with an upper side, a lower side for bone contact, two longitudinal sides, a longitudinal center line, a plurality of cylindrical screw holes extending from said upper to said lower side, said screw holes having curved edges, an area of said upper side around said screw holes being depressed with respect to the rest of said upper side, said depressed area having a curved upper edge, the upper edge of said depressed area having a curvature, $C_1$, which is less than 60% of the curvature, $C_2$, of the edge of said screw hole.

2. Bone plate according to claim 1, wherein said curvature $C_1$ is smaller than 10% of $C_2$.

3. Bone plate according to claim 1 wherein the depth of said depressed area gradually decreases toward said longitudinal center line of the bone plate.

4. Bone plate having an upper surface, a lower surface for bone contact, a longitudinal center line and a plurality of cylindrical screw holes extending through the plate, said screw holes having edges, the upper surface of the plate being dished out in the area around said screw holes to form elongated cavities, said cavities having side walls ascending steeply to said upper surface and sloping end walls tapering less steeply in the longitudinal direction from the screw holes upwardly to said upper surface, said upper surface being uninterrupted between said dished-out areas.

5. Bone plate according to claim 4 wherein the depth of said cavities gradually decreases toward said longitudinal center line of the bone plate.

6. Bone plate having an upper surface, a lower surface for bone contact, a longitudinal center line and a plurality of screw holes extending through the plate, said screw holes having edges, the upper surface of the plate being dished out in the area around said screw holes to form elongated cavities having side walls and sloping end walls tapering in the longitudinal direction from the edges of the screw holes upwardly to said upper surface, said side walls having a different slope from the slope of said end walls, said upper surface being uninterrupted between said cavities and wherein the depth of said cavities decreases towards said longitudinal center line.

7. Bone plate according to claim 6, wherein the lower surface of the bone plate has a concave shape.

8. Bone plate according to claim 7, and comprising transverse cuts on said lower surface of the bone plate.

9. Bone plate according to claim 6, wherein the depth of said cavities is in the range of 0.2 to 2.0 mm.

10. Bone plate according to claim 6 wherein the distance from the edge of said screw holes to said side walls is less than 1 mm.

11. Bone plate according to claim 6 wherein each of a plurality of screw holes associated with cavities is a cylindrical screw hole.

12. Bone plate having an upper surface, a lower surface for bone contact, a longitudinal center line, and a plurality of screw holes extending through the plate, said screw holes having edges, the upper surface of the plate being dished out in the areas around the screw holes to form elongated cavities having side walls, said side walls having edges, and sloping end walls tapering in the longitudinal direction from the edges of the screw holes upwardly to said upper surface, said upper surface being uninterrupted between said cavities, the depth of said cavities being such that the maximum stress under bending at the edges of said side walls is approximately equal to the maximum stress at the edges of said screw holes.

13. Bone plate according to claim 12, wherein said side walls are generally normal to said upper surface.

14. Bone plate according to claim 12 wherein each of a plurality of screw holes associated with cavities is a cylindrical screw hole.

15. Bone plate according to claim 12 wherein the depth of said cavities gradually decreases toward said longitudinal center line of the bone plate.

16. Bone plate having an upper surface, a lower surface for bone contact, a longitudinal center line and a plurality of cylindrical screw holes extending through the plate, said screw holes having edges, the upper surface of the plate being dished out in the area around said screw holes to form elongated cavities, said cavities having side walls ascending steeply to said upper surface and the cavity tapers less steeply adjacent its side walls in the longitudinal direction from the screw holes upwardly to said upper surface.

17. Bone plate according to claim 16 wherein the depth of said cavities gradually decreases toward said longitudinal center line of the bone plate.

* * * * *